United States Patent
Lawless et al.

(10) Patent No.: US 10,398,151 B1
(45) Date of Patent: Sep. 3, 2019

(54) METHOD AND APPARATUS OF USING ALCOHOL AND HIGH-PRESSURE PROCESSING (HPP) TO PRESERVE ALL-NATURAL BEVERAGES

(71) Applicants: Shawn Lawless, Cheshire, CT (US); Catherine Ragozzino, Haddam, CT (US)

(72) Inventors: Shawn Lawless, Cheshire, CT (US); Catherine Ragozzino, Haddam, CT (US)

( * ) Notice: Subject to any disclaimer, the term of this patent is extended or adjusted under 35 U.S.C. 154(b) by 0 days.

(21) Appl. No.: 16/422,664

(22) Filed: May 24, 2019

(51) Int. Cl.
| | |
|---|---|
| *A23B 4/00* | (2006.01) |
| *A23B 9/24* | (2006.01) |
| *A23B 9/32* | (2006.01) |
| *C12M 1/26* | (2006.01) |
| *C12M 1/34* | (2006.01) |

(52) U.S. Cl.
CPC .................. *A23B 4/00* (2013.01); *A23B 9/24* (2013.01); *A23B 9/32* (2013.01); *C12M 33/12* (2013.01); *C12M 41/40* (2013.01)

(58) Field of Classification Search
CPC .... A23B 4/00; A23B 9/24; A23B 9/32; A23B 7/14; C12M 33/12; C12M 41/40
USPC ................................. 426/590, 592
See application file for complete search history.

(56) References Cited

U.S. PATENT DOCUMENTS

| | | | |
|---|---|---|---|
| 6,033,701 A | 3/2000 | Hirsch | |
| 7,799,363 B2 | 9/2010 | Sherwood et al. | |
| 8,202,561 B2 | 6/2012 | Livaich | |
| 8,771,773 B2 | 7/2014 | Richter | |
| 8,993,023 B2 | 3/2015 | Legan et al. | |
| 2001/0038806 A1 | 11/2001 | Platz et al. | |
| 2007/0141203 A1* | 6/2007 | Cook | |
| 2007/0237865 A1 | 10/2007 | Love et al. | |
| 2010/0189860 A1 | 7/2010 | Tay et al. | |
| 2012/0269953 A1 | 10/2012 | Parker et al. | |
| 2015/0140177 A1 | 5/2015 | Kang et al. | |
| 2015/0351442 A1 | 12/2015 | Zhu et al. | |

OTHER PUBLICATIONS

High Pressure Processing (HPP) and Inspection Program Personnel (IPP) Verification Responsibilities, United States Department of Agriculture, Food Safety and Inspection Service, FSIS Directive 6120.2, May 23, 2012.
Hazard Analysis and Risk-Based Preventive Controls for Human Food: Draft Guidance for Industry, U.S. Food and Drug Administration, Office of Food Safety in the Center for Food Safety and Applied Nutrition, Chapter 4, Aug. 2016.
High-Pressure Processing Juice & Beverages, Avure Techologies Incorporated, May 2002.

* cited by examiner

*Primary Examiner* — Helen F Heggestad
(74) *Attorney, Agent, or Firm* — James R. McDaniel

(57) ABSTRACT

An all-natural fruit juice and alcohol composition, including a mixture of all-natural fruit juice and alcohol having a pH of less than or equal to 4.6, wherein the mixture has an alcohol content of 2-20% by volume, and wherein the mixture has been subjected to a high-pressure processing such that the mixture has been subjected to a pressure range of 70,000-95,000 psi for a time period of 1 to 5 minutes.

20 Claims, 1 Drawing Sheet

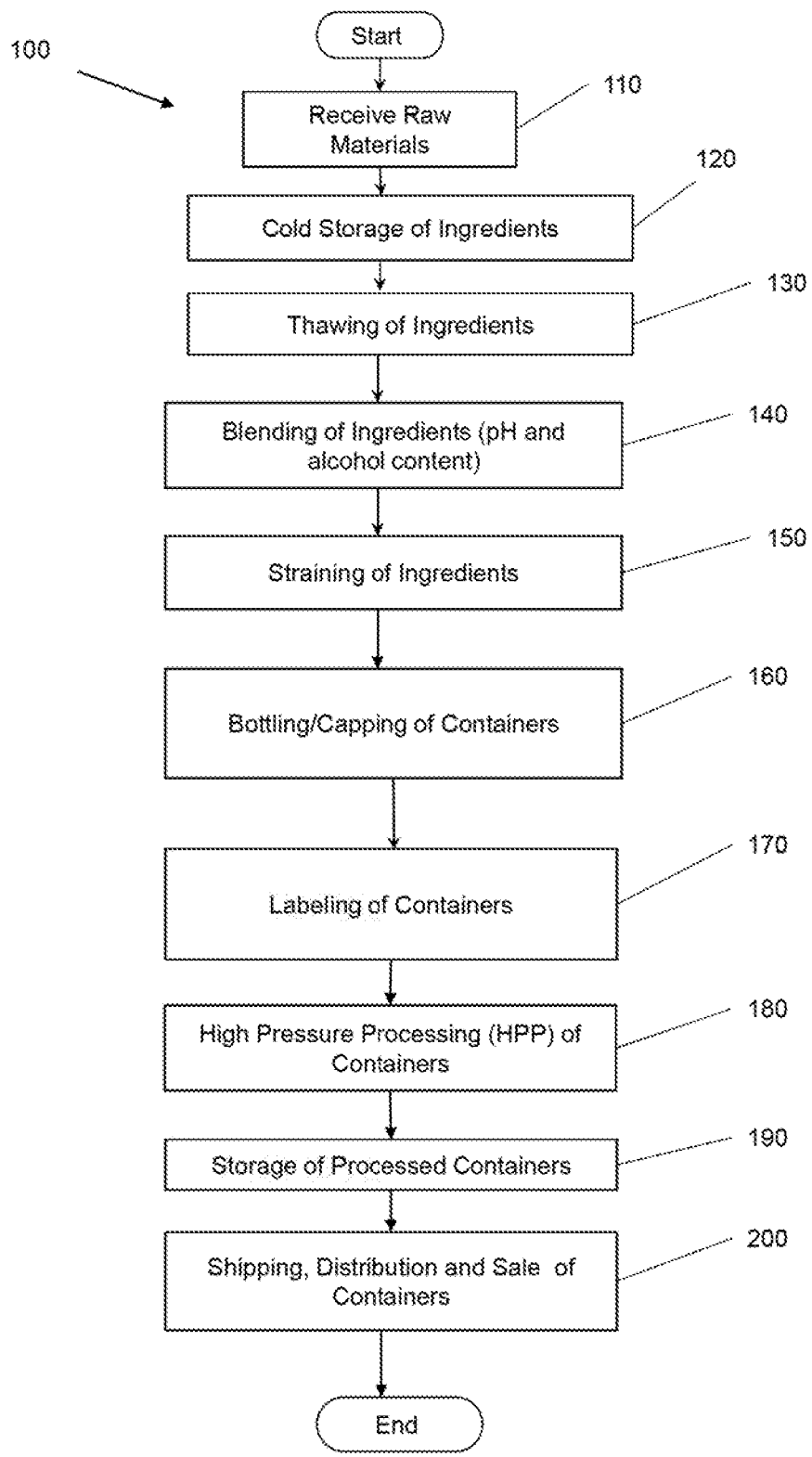

US 10,398,151 B1

METHOD AND APPARATUS OF USING ALCOHOL AND HIGH-PRESSURE PROCESSING (HPP) TO PRESERVE ALL-NATURAL BEVERAGES

FIELD OF THE INVENTION

The present invention is generally related to the preservation of all-natural beverages such as fruit juice by using alcohol and high-pressure processing (HPP) in order to remove any pathogens from the all-natural beverage and to provide a stable product that has a long shelf life without adversely affecting the taste, appearance, color, and the nutritional benefits of the all-natural beverage.

BACKGROUND OF THE INVENTION

Prior to the present invention, as set forth in general terms above and more specifically below, it is known, to employ various systems and methods to preserve food products. See for example, U.S. Pat. No. 6,033,701 by Hirsch, U.S. Pat. No. 7,799,363 by Sherwood et al., U.S. Pat. No. 8,202,561 by Livaich, U.S. Pat. No. 8,771,773 by Richter, U.S. Pat. No. 8,993,023 by Legan et al., U.S. Published Patent Application 2001/0038806 by Platz et al., U.S. Published Patent Application 2007/0237865 by Love et al., U.S. Published Patent Application 2010/0189860 by Tay et al., U.S. Published Patent Application 2012/0269953 by Parker et al., U.S. Published Patent Application 2015/0140177 by Kang et al., and U.S. Published Patent Application 2015/0351442 by Zhu et al. While these various systems and methods to preserve food products may have been generally satisfactory, there is nevertheless a need for a new and improved system and method of preserving all-natural beverages such as fruit juice by using alcohol and high-pressure processing (HPP) in order to remove any pathogens from the all-natural beverage and to provide a stable product that has a long shelf life without adversely affecting the taste, appearance, color, and the nutritional benefits of the all-natural beverage.

It is a purpose of this invention to fulfill this and other needs in the medicine art in a manner more apparent to the skilled artisan once given the following disclosure.

BRIEF SUMMARY OF THE INVENTION

A first aspect of the present invention is an all-natural fruit juice and alcohol composition, including a mixture of all-natural fruit juice and alcohol having a pH of less than or equal to 4.6, wherein the mixture has an alcohol content of 2-20% by volume, and wherein the mixture has been subjected to a high-pressure processing such that the mixture has been subjected to a pressure range of 70,000-95,000 psi for a time period of 1.0 to 5.0 minutes.

In one embodiment of the first aspect of the present invention, the all-natural fruit juice is selected from a group consisting of: lime juice; lemon juice; orange juice; other types of citrus juices; apple juice, grape juice; cranberry juice; tomato juice; other types of fruit juices; and blends of any of the juices.

In another embodiment of the first aspect of the present invention, the alcohol content is 6-15% by volume.

In a further embodiment of the first aspect of the present invention, the fruit juice has a pH of less than or equal to 4.6.

In a yet another embodiment of the first aspect of the present invention, the mixture has been subjected to a pressure of range of 80,000-90,000 psi.

In a still another embodiment of the first aspect of the present invention, the mixture has been subjected to a pressure of range of 80,000-90,000 psi for a time period of 2 minutes.

A second aspect of the present invention is a method of preparing an all-natural fruit juice and alcohol composition, including the steps of: introducing an amount of an all-natural fruit juice into a mixer, introducing an amount of an alcohol into the mixer; blending the mixture of all-natural fruit juice and alcohol while maintaining a pH of the mixture of all-natural fruit juice and alcohol at less than or equal to 4.6 and an alcohol content of 2-20% by volume; placing the blended mixture of all-natural fruit juice and alcohol in sealable containers; sealing the sealable containers containing the blended mixture of all-natural fruit juice and alcohol; transporting the sealed containers containing the blended mixture of all-natural fruit juice and alcohol to a high-pressure processing container; and subjecting the sealed containers containing the blended mixture of all-natural fruit juice and alcohol to a high-pressure processing such that the blended mixture has been subjected to a pressure range of 70,000-95,000 psi for a time period of 1.0 to 5.0 minutes.

In one embodiment of the second aspect of the present invention, the all-natural fruit juice is selected from a group consisting of: lime juice; lemon juice; orange juice; other types of citrus juices; apple juice, grape juice; cranberry juice; tomato juice; other types of fruit juices; and blends of any of the juices.

In another embodiment of the second aspect of the present invention, the alcohol content is 6-15% by volume.

In a further embodiment of the second aspect of the present invention, the fruit juice has a pH of less than or equal to 4.6.

In still another embodiment of the second aspect of the present invention, the mixture has been subjected to a pressure of range of 80,000-90,000 psi.

In yet another embodiment of the second aspect of the present invention, the mixture has been subjected to a pressure of range of 80,000-90,000 psi for a time period of 2 minutes.

In a still further embodiment of the second aspect of the present invention, the method further includes the step of straining the blended mixture of all-natural fruit juice and alcohol prior to placing the blended mixture of all-natural fruit juice and alcohol in the sealable containers.

A third aspect of the present invention is a method of preparing a beverage composition, wherein an all-natural fruit juice has been blended with alcohol and the composition has been subjected to high pressures in order to inactivate any pathogens or other microorganisms contained within the composition, including the steps of: introducing an amount of an all-natural fruit juice into a mixer introducing an amount of an alcohol into the mixer, blending the mixture of all-natural fruit juice and alcohol while maintaining a pH of the mixture of all-natural fruit juice and alcohol at less than or equal to 4.6 and an alcohol content of 2-20% by volume; placing the blended mixture of all-natural fruit juice and alcohol in sealable containers; sealing the sealable containers containing the blended mixture of all-natural fruit juice and alcohol; transporting the sealed containers containing the blended mixture of all-natural fruit juice and alcohol to a high-pressure processing container, and subjecting the sealed containers containing the blended mixture of all-natural fruit juice and alcohol to a high-pressure processing such that the blended mixture has been subjected to a pressure range of 70,000-95,000 psi for a time period of 1 to 5 minutes.

In one embodiment of the third aspect of the present invention, the all-natural fruit juice is selected from a group consisting of: lime juice; lemon juice; orange juice; other types of citrus juices; apple juice, grape juice; cranberry juice; tomato juice; other types of fruit juices; and blends of any of the juices.

In another embodiment of the third aspect of the present invention, the alcohol content is 6-15% by volume.

In a further embodiment of the third aspect of the present invention, the fruit juice has a pH of less than or equal to 4.6.

In still another embodiment of the third aspect of the present invention, the mixture has been subjected to a pressure of range of 80,000-90,000 psi.

In yet another embodiment of the third aspect of the present invention, the mixture has been subjected to a pressure of range of 80,000-90,000 psi for a time period of 2 minutes.

In a still further embodiment of the third aspect of the present invention, the method further includes the step of straining the blended mixture of all-natural fruit juice and alcohol prior to placing the blended mixture of all-natural fruit juice and alcohol in the sealable containers.

The preferred system and method of preserving all-natural beverages such as fruit juice by using alcohol and high-pressure processing (HPP), according to various embodiments of the present invention, offer the following advantages: ease of use; the ability to reduce the amount of pathogens contained within the all-natural beverage; increased shelf life of the processed product; improved stability of the processed product; decreased processing times; no reduction in the quality of the processed product; no reduction in the taste of the processed product; no reduction in the nutritional benefits of the processed product; no reduction in the appearance of the processed product; reduced need for refrigeration; and the ability to use a variety of different all-natural beverages. In fact, in many of the preferred embodiments, these advantages are optimized to an extent that is considerably higher than heretofore achieved in prior, known systems and methods for preserving all-natural beverages.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawing and in which:

FIG. 1 is a schematic illustration of the method of preserving all-natural beverages such as fruit juice by using alcohol and high-pressure processing (HPP), according to the present invention.

DETAILED DESCRIPTION OF THE PREFERRED EMBODIMENTS OF THE INVENTION

Consumers are drinking more all-natural beverages such as organic fruit juices because these juices taste better, have a just-squeezed appearance and are nutritional without using any preservatives or additives. However, in order to mass produce such all-natural beverages, the fruit juice cannot be heat-treated since the heat treatment will adversely affect the taste and the nutritional benefits of the organic fruit juice. In order to address this problem, it is known to use high-pressure processing (HPP) in the processing of food products such as beverages.

During HPP, the beverage is subjected to very high pressures (up to 100,000 psi). These high pressures inactivate the pathogens or other microorganisms that may be found in the beverages. It has also been found that these high pressures do not adversely affect the taste, texture, color and nutritional benefits of the beverages. While these prior, known HPP systems and methods are generally satisfactory in processing beverages, the processed beverages are not shelf stable and, therefore, must be refrigerated. Consequently, it is desirable to create a system and method that is capable of preserving of all-natural beverages such as fruit juice by using alcohol and high-pressure processing (HPP) in order to remove any pathogens from the all-natural beverage and to provide a stable product that has a long shelf life without the need for refrigeration and without adversely affecting the taste and the nutritional benefits of the all-natural beverage.

Referring now to FIG. 1, there is illustrated a method 100 of preserving of all-natural beverages such as fruit juice by using alcohol and high-pressure processing (HPP). As will be explained hereinafter in greater detail, the method 100 of processing beverages is capable of preserving all-natural beverages such as fresh fruit juice or frozen fruit juice that has been thawed by using alcohol and high-pressure processing (HPP) in order to remove any pathogens from the all-natural beverage and to provide a stable product that has a long shelf life without the need for refrigeration and without adversely affecting the taste and the nutritional benefits of the all-natural beverage.

With respect to the presently disclosed invention, the following should be considered relative to the organic, all-natural juice component of the system and method. It is to be understood that non-organic fruit juice could also be used. That is, the all-natural juice (whether it is organic or non-organic) is preferably prepared and packaged according to conventional all-natural juice production techniques. Also, the all-natural juice is inspected by the beverage packager prior to and after the packaging of the all-natural juice, according to well-known processes and procedures. After the all-natural juice has been conventionally prepared and packaged, the packaged all-natural juice is then ready to be processed according to the present invention, as will be described in greater detail below.

Also, the following should be considered relative to the alcohol component of the system and method. That is, the alcohol is preferably any suitable distilled alcohol (such as alcohols (including ethanol (or ethyl alcohol)) distilled from wine or other fermented fruit, a plant juice or a starchy material such as or potatoes), beer or wine that are suitable for human consumption. It is to be understood that cannabidiol (CBD) can also be added as another component of the system and method. It is to be further understood that CBD may be used in addition to the alcohol component since the alcohol is needed to ensure ambient temperature stability of the processed product.

Method of Processing the all-Natural Beverage Using Alcohol and High-Pressure Processing (HPP)

The following example is provided merely for illustrating the present invention and is not to be intended as limiting the scope of protection of the appended claims.

Example 1

1.) Composition
  An all-natural beverage such as fruit juice has been has been formulated with the following composition:
   a.) Types of all-natural juices or juice blends include, but are not limited to: lime juice, lemon juice, orange juice, other types of citrus juices, apple juice, grape juice, cranberry juice, tomato juice, other types of fruit juices, and blends of any of these juices.
   b.) Batch size of all-natural beverage such as fruit juice could be between about 100 and 1,000 gallons;
      i. Preferably, the batch size will be between about 500 and 1,000 gallons of all-natural beverage; and
   c.) The alcohol range level must be at least 2% to 20% of the total volume of the batch size
      i. Preferably, the alcohol range level will be between about 5%-16% based on comparable alcohol-infused drinks.
2.) Method 100 of FIG. 1)
  The following steps were carried out:
  Step 110—Receive Raw Materials
  The raw materials are received from the raw material producers at the processing plant. In particular, the raw materials include, but are not limited to, the all-natural beverage such as fruit juice and the alcohol such any suitable distilled alcohol (such as alcohols distilled from wine or other fermented fruit, a plant juice or a starchy material such as or potatoes), beer or wine that are suitable for human consumption. It is to be understood that the producers of the raw materials must ensure that the raw materials do not contain any allergens. It is to be further understood that the raw materials should be conventionally inspected when received by the personnel at the processing plant to ensure that the raw materials comply with the desired raw material specifications and food safety standards.

Step 120—Cold Storage of Raw Materials
  After the raw materials have been received and inspected by the personnel at the processing plant, the raw materials are stored in cold storage. In particular, the raw materials are conventionally stored in a refrigerated warehouse (at a temperature of 40° F. or less) that is continuously monitored to ensure product safety. Furthermore, the raw materials are placed on conventional storage racks in sealed, unopened containers so that the presence of allergens into the raw materials is substantially reduced or eliminated. It is to be understood that any raw material container that is found to be damaged or leaking during storage will be inspected to determine if the raw material contained within the damaged or leaking container is safe to be further processed. If the raw material is not safe to be further processed, the damaged raw material is then properly disposed.

Step 130—Thawing of Ingredients
  While some of the raw materials may be transported to the processing plant as chilled beverages, other raw materials such as all-natural fruit juice may be frozen by the beverage producer in order to be able to properly transport the beverage from its processing location to a further processing plant. In particular, all-natural fruit juice that is processed overseas may need to be frozen so that the all-natural fruit juice will not spoil and will retain its fresh, just-squeezed appearance, flavor, texture and nutritional benefits.
  If the raw material does arrive at the processing plant in a frozen state, the frozen raw materials are also conventionally stored in the refrigerated warehouse (at a temperature of 40° F. or less) that is continuously monitored to ensure product safety. Furthermore, the raw materials are placed on conventional storage racks in sealed, unopened containers so that frozen raw materials can properly thaw out and so that the presence of allergens into the raw materials is substantially reduced or eliminated. It is to be understood that any frozen, raw material container that is found to be damaged or leaking during storage will be inspected to determine if the frozen or thawed, raw material contained within the damaged or leaking container is safe to be further processed. If the raw material is not safe to be further processed, the damaged raw material is then properly disposed.

Step 140—Blending of Ingredients
  During this step, the all-natural beverage such as fruit juice and alcohol such as grain alcohol or other similar distilled alcohols that are suitable for human consumption are combined together in batches in a conventional, industrial batch mixer (not shown) for mixing large quantities of beverage compositions. In particular, after the batch mixer has been conventionally cleaned and sanitized, the all-natural beverage is conventionally introduced into the batch mixer. It is to be understood that the all-natural beverage passes through a conventional containment screen (not shown) in order to prevent any foreign material from entering into the batch mixer. It is to be further understood that the pH of the all-natural beverage is conventionally tested to ensure that the pH is at or below 4.6 in order to reduce the likelihood of any pathogen or other microorganism growth in the all-natural beverage. Also, the alcohol content of the all-natural beverage is conventionally measured.
  After the all-natural beverage has been introduced into the batch mixer, the alcohol is conventionally introduced into the batch mixer. In particular, the alcohol passes through the conventional containment screen (not shown) in order to prevent any foreign material from entering into the batch mixer. It is to be further understood that the alcohol volume (in terms of percentage of alcohol to the total volume of liquid in the batch mixer) is measured. In particular, the alcohol percentage should be 2-20% by volume with the preferred alcohol percentage range being 6-15% by volume. It is to be further understood that the all-natural beverage and alcohol composition must have a final pH (after high-pressure processing) that is at or below 4.6 in order to reduce the likelihood of any pathogen or other microorganism growth in the all-natural beverage and alcohol composition.
  A unique aspect of the present invention is the addition of the alcohol component to the all-natural beverage and alcohol composition. As discussed above, the use of HPP to process beverages is well known. However, as discussed above, it has been found that beverages subjected to HPP typically are not shelf stable and, therefore, must be refrigerated. The addition of alcohol in an alcohol percentage range of 5-20% by volume has been found by the inventors of the present invention to eliminate the need to refrigerate the processed product. This allows the processed product of the present invention to be shipped anywhere in the world without the need for refrigeration. Furthermore, the addition of the alcohol will also aid in the reduction of any pathogens or other harmful microorganisms originally contained within the all-natural beverage.
  Once the proper amounts of all-natural beverage and alcohol have been introduced into the batch mixer, the batch mixer then conventionally mixes the materials for approximately 3-7 minutes so that the all-natural beverage and alcohol components have been property and evenly blended.

Step 150—Straining of Ingredients
  After the all-natural beverage and alcohol have been properly and evenly blended, the all-natural beverage and alcohol composition is conventionally strained. In particular, the blended composition of all-natural beverage and alcohol are strained through a conventional containment screen (not shown) to ensure that no contaminants or other foreign materials (such as glass, plastic, rocks, etc.) are sent to the bottling/capping area. Furthermore, the blended composition of all-natural beverage and alcohol is conventionally, visually inspected to ensure that no contaminants have passed through the containment screen.

Step 160—Bottling/Capping of Containers

Once the all-natural beverage and alcohol are conventionally strained, the strained all-natural beverage and alcohol are then conventionally bottled/capped. In particular, any suitable HPP-compatible beverage containers such as food grade polyethylene terephthalate (PET) containers are filled with the all-natural beverage and alcohol composition. It is to be understood that prior to filling the containers with the composition of all-natural beverage and alcohol, the food grade containers and the container caps (if used) are conventionally inspected to ensure that the containers and caps do not contain any contaminants. Also, the food grade containers and the caps (if used) are then conventionally cleaned and sterilized prior to being filled with the all-natural beverage and alcohol composition. After the food grade containers have been properly filled with the desired amount of all-natural beverage and alcohol composition, the containers are conventionally sealed or capped so that no pathogens can be later introduced into the packaged all-natural beverage and alcohol composition. It is to be understood that the containers can be in the form of bottles, stand-up pouches, large bulk bags or the like.

Step 170—Labeling of Filled Containers

After the food grade containers have been properly filled with the desired amount of all-natural beverage and alcohol composition and the containers have been conventionally sealed or capped, the desired labeling is conventionally applied to the filled containers, if needed. If the containers are already printed with the labeling such as individual, stand-up pouches which a pre-printed with labels, there may not be a need to apply any further labels after the pouches have been filled. It is to be understood that the all-natural beverage and alcohol composition contained within the container must be labeled with the correct information about the all-natural beverage and alcohol composition contained within the container. In particular, the correct ingredients must be labeled. It is to be further understood that the labeled containers will be visually inspected to ensure that the labels are not misprinted or that the filled containers are not mislabeled.

Step 180—High-Pressure Processing (HPP) of Filled Containers

Once the food grade containers have been filled with the desired amount of all-natural beverage and alcohol composition, the containers have been conventionally sealed or capped and the desired labeling has been attached to the food grade containers, the filled, sealed containers are then processed under high-pressure in a conventional high-pressure processing apparatus (not shown). In particular, filled, sealed containers are placed within the high-pressure processing apparatus. The high-pressure processing apparatus is conventionally closed or sealed. The filled, sealed containers are then subjected to a high-pressure (in a range of 70,000-95,000 psi, preferably in a range of 80,000-90,000 psi) for a time period of 1.5 to 2.5 minutes, preferably for a time period of 2 minutes. It is to be understood that the filled, sealed containers must be kept at this high-pressure range for this period of time in order to achieve the desired 5 log reduction of each bacteria.

It is to be understood that if a particular cycle fails (either the pressure is not maintained for the time period or the time is not properly measured), the high-pressure processing apparatus will conventionally stop and a failure notice will be sent to the processing plant personnel. That particular cycle of processing will then be inspected to determine if the filled, sealed containers and the product contained within those containers that was being processed during that particular cycle have been adversely affected and should be discarded.

Another unique aspect of the present invention is the use of the high-pressures in conjunction with the all-natural beverage and alcohol composition. In particular, the all-natural beverage and alcohol composition is subjected to the very high pressures which result in the inactivation of the spoilage microorganisms such as yeast and mold and other undesirable pathogens. Also, the high pressures reduce the amount of enzymatic activity in the all-natural beverage and alcohol composition. However, the high pressures do not change the taste, appearance, or color of the all-natural beverage and alcohol composition and do not adversely affect the nutritional benefits of the all-natural beverage and alcohol composition. Furthermore, the high pressures reduce the need to sterilize the food grade containers since the reduction of the microorganisms in the all-natural beverage and alcohol composition and the food grade container takes places during the high-pressure processing (HPP).

Step 190—Storage of HPP Processed Containers

After the filled, sealed containers have been processed using HPP, the processed containers are visually inspected to see if any of the processed containers experienced leaks or other container failures due to the high-pressure processing. If any such containers are found, those particular containers will be conventionally discarded. Those containers that have been properly processed are then conventionally transported to a conventional storage facility. In particular, the processed containers are stored on storage racks in the storage facility at ambient/room temperature (between 60 and 75° F.). It is to be understood that the stored containers are periodically, visually inspected to ensure that none of the stored, processed containers have experienced any sort of leakage or failure. If a processed container is discovered to have a failure or leakage, that particular container is then properly disposed of by conventional methods.

Step 200—Shipping, Distribution and Sale of Processed Containers

Upon receipt of an order for processed containers of the all-natural beverage and alcohol composition, the order is conventionally processed by the personnel at the storage facility. The order is then conventionally collected and visually inspected to ensure that no visual contaminants are in any of the processed containers.

Once the order has been collected and inspected, the order to conventionally distributed to the purchaser and the processed containers are subsequently sold.

3.) Test Results

The following tests were carried out:

a.) Real-Time Storage Trial Tests i. Objective—The test objective is to understand the relationship between all-natural beverages and alcohol and address the possibility of any synergistic effects. Samples were prepared according the method, as described above.

| Product | Ingredients | % Alcohol | Production Date |
| --- | --- | --- | --- |
| Lemonade | Lemon, Agave, Water, Vodka | 6.00 | Feb. 8, 2019 |
| Limeade | Lime, Seltzer, Tequila, Agave | 13.33 | Mar. 15, 2019 |
| Cosmopolitan | Vodka, Cranberry, Lime, Sugar, Triple Sec | 14.99 | Mar. 15, 2019 |
| Lemonade Control | Lemon, Agave, Water, Vodka | 6.00 | Apr. 1, 2019 |
| Limeade Control | Lime, Seltzer, Tequila, Agave | 13.33 | Apr. 1, 2019 |

| Product | HPP Date |
| --- | --- |
| Lemonade | Feb. 18 2019 |
| Limeade | Mar. 15, 2019 |
| Cosmopolitan | Mar. 15, 2019 |
| Lemonade Control | None |
| Limeade Control | None |

| Product | Check 1 | Check 2 | Check 3 | Check 4 |
| --- | --- | --- | --- | --- |
| Lemonade | Feb. 11, 2019 | Feb. 17, 2019 | Feb. 24, 2019 | Mar. 3, 2019 |
| Limeade | Mar. 19, 2019 | Apr. 3, 2019 | Apr. 18, 2019 | May 18, 2019 |
| Cosmopolitan | Mar. 19, 2019 | Apr. 3, 2019 | Apr. 18, 2019 | May 18, 2019 |
| Lemonade Control | May 7, 2019 | | | |
| Limeade Control | May 7, 2019 | | | |

| Product | Check 5 | Check 6 | Notes |
| --- | --- | --- | --- |
| Lemonade | Apr. 11, 2019 | May 11, 2019 | 88 Days and still showing good taste and micros |
| Limeade | Jun. 18, 2019 | | 53 Days and still showing good taste and micros |
| Cosmopolitan | Jun. 18, 2019 | | 53 Days and still showing good taste and micros |
| Lemonade Control | | | 34 day taste was rancid; samples sent to lab to confirm |
| Limeade Control | | | 34 day taste was rancid; samples sent to lab to confirm | ii. Results—The tests demonstrate the interrelationship between high-pressure processing (HPP) and a composition of an all-natural beverage and alcohol with the effects of pressure and time.

iii. The results demonstrate that the compositions of all-natural beverages made with alcohol and not processed using HPP spoil very quickly after production. In particular, the compositions made with all-natural beverages and varying amounts of alcohol show that between a range of 6% alcohol to 14.99% alcohol, the fruit juice mixed with alcohol was not shelf stable. In fact, within 10 days of production, the containers containing the compositions of all-natural beverages made with alcohol and not processed using HPP showed signs of bloating and rancid smell.

iv. Across all of the compositions of all-natural beverages made with alcohol and processed using HPP (processed at 87,000 PSI for 180 seconds) retained all of their micro and sensory qualities since the date of production.

v. These tests demonstrate that alcohol alone at typical consumption percentages of between 8% and 10% is not enough to preserve an all-natural fruit juice blend. High pressure processing (HPP) is needed to produce a product that can retain its qualities through a distribution process.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising," "including," "containing," etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved system and method of preserving all-natural beverages such as fruit juice by using alcohol and high-pressure processing (HPP), according to various embodiments of the present invention, offer the following advantages: ease of use; the ability to reduce the amount of pathogens contained within the all-natural beverage; increased shelf life of the processed product; improved stability of the processed product; decreased processing times; no reduction in the quality of the processed product; no reduction in the taste of the processed product; no reduction in the nutritional benefits of the processed product; no reduction in the taste of the processed product; reduced need for refrigeration; and the ability to use a variety of different all-natural beverages. In fact, in many of the preferred embodiments, these factors of ease of use, the ability to reduce the amount of pathogens contained within the all-natural beverage, increased shelf life of the processed product, improved stability of the processed product, decreased processing times, no reduction in the quality of the processed product, no reduction in the taste of the processed product, no reduction in the nutritional benefits of the processed product, no reduction in the taste of the processed product, reduced need for refrigeration, and the ability to use a variety of different all-natural beverages are optimized to an extent that is considerably higher than heretofore achieved in prior, known systems and methods for preserving all-natural beverages.

What is claimed is:

1. An all-natural shelf-stable fruit juice and alcohol composition, comprising:
   a mixture of all-natural fruit juice and alcohol having a pH of less than or equal to 4.6,
   wherein the mixture has an alcohol content of 2-20% by volume; and wherein the mixture has been subjected to a high-pressure processing such that the mixture has been subjected to a pressure range of 70,000-95,000 psi for a time period of 1 to 5 minutes.

2. The composition, according to claim 1, wherein the all-natural fruit juice is selected from a group consisting of:
lime juice; lemon juice; orange juice; apple juice, grape juice; cranberry juice; tomato juice; and blends of any of the juices.

3. The composition, according to claim 1, wherein the alcohol content is 6-15% by volume.

4. The composition, according to claim 1, wherein the fruit juice has a pH of less than or equal to 4.6.

5. The composition, according to claim 1, wherein the mixture has been subjected to a pressure of range of 80,000-90,000 psi.

6. The composition, according to claim 5, wherein the mixture has been subjected to a pressure of range of 80,000-90,000 psi for a time period of 2 minutes.

7. A method of preparing an all-natural fruit juice and alcohol composition, comprising the steps of:
introducing an amount of an all-natural fruit juice into a mixer;
introducing an amount of an alcohol into the mixer,
blending the mixture of all-natural fruit juice and alcohol while maintaining a pH of the mixture of all-natural fruit juice and alcohol at less than or equal to 4.6 and an alcohol content of 2-20% by volume;
placing the blended mixture of all-natural fruit juice and alcohol in sealable containers;
sealing the sealable containers containing the blended mixture of all-natural fruit juice and alcohol;
transporting the sealed containers containing the blended mixture of all-natural fruit juice and alcohol to a high-pressure processing container; and
subjecting the sealed containers containing the blended mixture of all-natural fruit juice and alcohol to a high-pressure processing such that the blended mixture has been subjected to a pressure range of 70,000-95,000 psi for a time period of 1 to 5 minutes.

8. The method of preparing an all-natural fruit juice and alcohol composition, according to claim 7, wherein the all-natural fruit juice is selected from a group consisting of:
lime juice; lemon juice; orange juice; apple juice, grape juice; cranberry juice; tomato juice; and blends of any of the juices.

9. The method of preparing an all-natural fruit juice and alcohol composition, according to claim 7, wherein the alcohol content is 6-15% by volume.

10. The method of preparing an all-natural fruit juice and alcohol composition, according to claim 7, wherein the fruit juice has a pH of less than or equal to 4.6.

11. The method of preparing an all-natural fruit juice and alcohol composition, according to claim 7, wherein the mixture has been subjected to a pressure of range of 80,000-90,000 psi.

12. The method of preparing an all-natural fruit juice and alcohol composition, according to claim 11, wherein the mixture has been subjected to a pressure of range of 80,000-90,000 psi for a time period of 2 minutes.

13. The method of preparing an all-natural fruit juice and alcohol composition, according to claim 7, wherein the method is further comprised of the step of:
straining the blended mixture of all-natural fruit juice and alcohol prior to placing the blended mixture of all-natural fruit juice and alcohol in the sealable containers.

14. A method of preparing a beverage composition, wherein an all-natural fruit juice has been blended with alcohol and the composition has been subjected to high pressures in order to inactivate any pathogens or other microorganisms contained within the composition, comprising the steps of:
introducing an amount of an all-natural fruit juice into a mixer;
introducing an amount of an alcohol into the mixer,
blending the mixture of all-natural fruit juice and alcohol while maintaining a pH of the mixture of all-natural fruit juice and alcohol at less than or equal to 4.6 and an alcohol content of 2-20% by volume;
placing the blended mixture of all-natural fruit juice and alcohol in sealable containers;
sealing the sealable containers containing the blended mixture of all-natural fruit juice and alcohol;
transporting the sealed containers containing the blended mixture of all-natural fruit juice and alcohol to a high-pressure processing container; and
subjecting the sealed containers containing the blended mixture of all-natural fruit juice and alcohol to a high-pressure processing such that the blended mixture has been subjected to a pressure range of 70,000-95,000 psi for a time period of 1 to 5 minutes.

15. The method of preparing a beverage composition, according to claim 14, wherein the all-natural fruit juice is selected from a group consisting of:
lime juice; lemon juice; orange juice; apple juice, grape juice; cranberry juice; tomato juice; and blends of any of the juices.

16. The method of preparing a beverage composition, according to claim 14, wherein the alcohol content is 6-15% by volume.

17. The method of preparing a beverage composition, according to claim 14, wherein the fruit juice has a pH of less than or equal to 4.6.

18. The method of preparing a beverage composition, according to claim 14, wherein the mixture has been subjected to a pressure of range of 80,000-90,000 psi.

19. The method of preparing a beverage composition, according to claim 18, wherein the mixture has been subjected to a pressure of range of 80,000-90,000 psi for a time period of 2 minutes.

20. The method of preparing a beverage composition, according to claim 14, wherein the method is further comprised of the step of:
straining the blended mixture of all-natural fruit juice and alcohol prior to placing the blended mixture of all-natural fruit juice and alcohol in the sealable containers.

* * * * *